(12) United States Patent
Callahan et al.

(10) Patent No.: US 12,721,692 B2
(45) Date of Patent: Sep. 1, 2026

(54) PACKAGING FACILITATING STERILE CONNECTIONS

(71) Applicant: CareFusion 303, Inc., San Diego, CA (US)

(72) Inventors: Ryan Callahan, Long Beach, CA (US); Leah Paige Gaffney, Orange, CA (US); Siddarth Shevgoor, Mission Viejo, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 18/787,248

(22) Filed: Jul. 29, 2024

(65) Prior Publication Data

US 2026/0026909 A1 Jan. 29, 2026

(51) Int. Cl.
*A61B 50/39* (2016.01)
*A61B 50/30* (2016.01)

(52) U.S. Cl.
CPC ...... *A61B 50/39* (2016.02); *A61B 2050/3009* (2016.02)

(58) Field of Classification Search
CPC . A61B 50/39; A61B 2050/3009; A61M 5/002
USPC .............................. 206/363–365, 477; 220/8
See application file for complete search history.

(56) References Cited

U.S. PATENT DOCUMENTS 4,106,621 A * 8/1978 Sorenson ............. B65D 75/328 229/125.35
5,133,454 A * 7/1992 Hammer ............. A61M 5/3205 206/364
5,407,070 A * 4/1995 Bascos .................. A61M 5/002 206/467
5,713,856 A 2/1998 Eggers et al.
6,874,522 B2 4/2005 Anderson et al.
7,004,934 B2 2/2006 Vaillancourt
7,040,598 B2 5/2006 Raybuck
7,153,296 B2 12/2006 Mitchell
7,350,764 B2 4/2008 Raybuck
7,396,051 B2 7/2008 Baldwin et al.
7,763,013 B2 7/2010 Baldwin et al.
7,766,394 B2 8/2010 Sage et al.
7,794,675 B2 9/2010 Lynn
(Continued)

FOREIGN PATENT DOCUMENTS

CA 2318624 A1 7/1999
EP 1678070 A2 7/2006
(Continued)

OTHER PUBLICATIONS

International Search Report and Written Opinion for Application No. PCT/US2025/039102, dated Nov. 4, 2025, 10 pages.
(Continued)

*Primary Examiner* — Rafael A Ortiz
(74) *Attorney, Agent, or Firm* — MASCHOFF BRENNAN

(57) ABSTRACT

Packaging may be designed to allow for the forced connection of separate parts without breaching the sterile barrier of the packaging. A component holder housed within sterile packaging may hold device parts such that the device parts can shipped and stored separated and can be pushed together to create a sterile connection between the parts while the parts are housed within the packaging.

17 Claims, 3 Drawing Sheets

(56) References Cited

U.S. PATENT DOCUMENTS 7,803,139 B2 9/2010 Fangrow, Jr.
7,803,140 B2 9/2010 Fangrow, Jr.
7,815,614 B2 10/2010 Fangrow, Jr.
7,918,243 B2 4/2011 Diodati et al.
7,998,134 B2 8/2011 Fangrow et al.
8,113,348 B2 * 2/2012 Foster .................... A61B 50/20 206/478
8,123,738 B2 2/2012 Vaillancourt
8,142,418 B2 3/2012 Mcmichael et al.
8,211,069 B2 7/2012 Fangrow, Jr.
8,261,910 B2 * 9/2012 Guenter ............... A61C 8/0087 206/363
8,262,628 B2 9/2012 Fangrow, Jr.
8,361,408 B2 1/2013 Lynn
8,480,968 B2 7/2013 Lynn
8,777,908 B2 7/2014 Fangrow, Jr.
8,777,909 B2 7/2014 Fangrow, Jr.
8,795,256 B1 8/2014 Smith
8,888,758 B2 11/2014 Mansour
8,899,267 B2 12/2014 Diodati et al.
8,910,919 B2 12/2014 Bonnal et al.
8,974,425 B2 3/2015 Tachizaki et al.
8,974,437 B2 3/2015 Williams et al.
9,114,242 B2 8/2015 Fangrow et al.
9,126,028 B2 9/2015 Fangrow et al.
9,126,029 B2 9/2015 Fangrow et al.
9,192,753 B2 11/2015 Lopez et al.
9,234,616 B2 1/2016 Carrez et al.
9,358,379 B2 6/2016 Fangrow, Jr.
9,433,769 B2 9/2016 Bayly
9,468,749 B2 10/2016 Mansour et al.
9,492,649 B2 11/2016 Carrez et al.
9,636,492 B2 5/2017 Fangrow, Jr.
9,724,504 B2 8/2017 Fangrow, Jr. et al.
9,724,505 B2 8/2017 Williams et al.
9,861,805 B2 1/2018 Dennis et al.
9,933,094 B2 4/2018 Fangrow
9,974,939 B2 5/2018 Fangrow, Jr.
9,974,940 B2 5/2018 Fangrow, Jr.
10,029,086 B2 7/2018 Nowak et al.
10,156,306 B2 12/2018 Fangrow
10,173,045 B2 1/2019 Mansour
10,179,203 B1 1/2019 Huslage et al.
10,315,025 B2 6/2019 Phillips et al.
10,398,887 B2 9/2019 Fangrow, Jr. et al.
10,441,507 B2 10/2019 Sanders
10,518,078 B2 12/2019 Stjernberg Bejhed et al.
10,569,073 B2 2/2020 Hallisey et al.
10,625,068 B2 4/2020 Leuthardt et al.
10,655,768 B2 5/2020 Jones et al.
10,697,570 B2 6/2020 Fangrow
10,744,315 B2 8/2020 Sanders
10,842,982 B2 11/2020 Fangrow, Jr.
10,857,346 B2 12/2020 Dennis et al.
10,864,362 B2 12/2020 Jones et al.
10,881,847 B2 1/2021 Lynn
11,168,818 B2 11/2021 Fangrow
11,207,514 B2 12/2021 Kakinoki
11,235,135 B2 2/2022 Tsai
11,273,297 B2 3/2022 Kakinoki
11,484,471 B2 11/2022 Sanders
11,491,084 B2 11/2022 Ueda et al.
2004/0215158 A1 10/2004 Anderson
2005/0033237 A1 * 2/2005 Fentress ............ A61M 25/0014 604/165.03
2005/0090805 A1 4/2005 Shaw et al.
2006/0042977 A1 * 3/2006 Sandel .................. A61B 50/33 206/370
2006/0129109 A1 6/2006 Shaw et al.
2007/0088292 A1 4/2007 Fangrow, Jr.
2007/0088293 A1 4/2007 Fangrow, Jr.
2007/0088294 A1 4/2007 Fangrow, Jr.
2007/0225635 A1 9/2007 Lynn
2008/0039803 A1 2/2008 Lynn
2009/0082752 A1 3/2009 Pipelka
2011/0106046 A1 5/2011 Hiranuma
2014/0249487 A1 9/2014 Lynn
2014/0330254 A1 11/2014 Rosenberger et al.
2016/0000363 A1 1/2016 Jones et al.
2017/0088325 A1 3/2017 Webster et al.
2018/0200147 A1 7/2018 Sanders
2019/0184152 A1 6/2019 Kakinoki
2019/0282797 A1 9/2019 Tsai
2020/0113784 A1 4/2020 Lopez et al.
2020/0179672 A1 6/2020 Kakinoki
2020/0215319 A1 7/2020 Fangrow, Jr. et al.
2020/0284385 A1 9/2020 Fangrow
2020/0323734 A1 10/2020 Ueda et al.
2020/0338331 A1 10/2020 Sanders
2021/0069484 A1 3/2021 Tsai
2021/0077803 A1 3/2021 Lynn
2021/0252267 A1 8/2021 Fangrow, Jr.
2021/0388926 A1 12/2021 Martin et al.
2021/0393938 A1 12/2021 Lynn et al.
2022/0260189 A1 8/2022 Deuse
2022/0282814 A1 9/2022 Fangrow
2024/0358875 A1 * 10/2024 Malik .................... A61B 50/33

FOREIGN PATENT DOCUMENTS

EP 1517723 B1 1/2007
EP 1622675 B1 8/2009
EP 2144634 A1 1/2010
EP 2298407 A1 3/2011
EP 2694132 A1 2/2014
EP 2562456 B1 6/2014
EP 2782633 A1 10/2014
EP 1842002 B1 4/2015
EP 2736582 B1 5/2015
EP 2089094 B1 1/2016
EP 2219721 B1 12/2017
EP 2753396 B1 12/2017
EP 2736584 B1 4/2018
EP 3305361 A1 4/2018
EP 2271398 B1 11/2018
EP 2480281 B1 11/2018
EP 2790750 B1 11/2018
EP 2331191 B1 3/2019
EP 3079756 B1 3/2019
EP 2121114 B1 5/2019
EP 2719419 B1 5/2019
EP 2956204 B1 8/2019
EP 3421077 B1 8/2019
EP 3530313 A1 8/2019
EP 3538201 A1 9/2019
EP 3570807 A1 11/2019
EP 3570809 A1 11/2019
EP 2536463 B1 4/2020
EP 3381505 B1 5/2020
EP 3538201 B1 5/2020
EP 1904152 B1 12/2020
EP 2150307 B1 12/2020
EP 3313490 B1 1/2021
EP 3760275 A1 1/2021
EP 3851155 A1 7/2021
EP 3517164 B1 9/2021
EP 3954355 A1 2/2022
EP 3960229 A1 3/2022
EP 3973044 A1 3/2022
EP 3305361 B1 5/2022
EP 3134052 B1 8/2022
EP 3530313 B1 8/2022
WO WO-2021099437 A1 5/2021
WO WO-2021180675 A1 9/2021
WO WO-2021252197 A1 12/2021
WO WO-2022042956 A1 3/2022
WO WO-2022149339 A1 7/2022
WO WO-2022207560 A1 10/2022

OTHER PUBLICATIONS

Bangert, Bill, "Shorter times to blood transfusion associated with decreased death risk in trauma patients", Medical Xpress, Apr. 14,

(56) References Cited

OTHER PUBLICATIONS 2016, https://medicalxpress.com/news/2016-04-shorter-blood-transfusion-decreased-death.html.
ICUMEDICAL, "ChemoClave™ Needlefree Close System Transfer Device (CSTD)", date unknown, https://www.icumed.com/products/oncology/closed-system-transfer-devices/chemoclave.
ICUMEDICAL, "ChemoLock™ Needlefree Closed System Transfer Device (CSTD)", date unknown, https://www.icumed.com/products/oncology/closed-system-transfer-devices/chemolock.
IVTEAM, "Force-activated separation IV connectors", 2022, Retrieved from the internet https://www.ivteam.com/intravenous-literature/force-activated-separation-iv-connectors/ [Last retrieved Jan. 13, 2023].
Lineus Medical, SafeBreak Product Features and Benefits Brochure, May 2021, mkg 0058 5/21 Rev. 02.
PRZen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].
Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.
Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].
Tribology, "Coefficient of friction, Rolling resistance and Aerodynamics", date unknown, https://www.tribology-abc.com/abc/cof.htm.

* cited by examiner

PACKAGING FACILITATING STERILE CONNECTIONS

FIELD OF THE INVENTION

The present disclosure generally relates to packaging, and, in particular, sterile packing for fluid connectors.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. In many cases, multiple fluid connector pieces need to be connected to form the complete fluid infusion system. Connecting multiple connector pieces can introduce the possibility of contamination.

Shipping connection parts in sterile packaging can reduce the chance of contamination and eliminate the need for antimicrobial swabbing or other cleaning before setup. However, certain devices, such as force activated separation devices (FASD), cannot be shipped in a fully prepared state and require the user to make certain connections before using. Additionally, unconnected storage of the parts may be required in order to ensure no performance degradation of the parts.

SUMMARY

One or more embodiments of the present disclosure are directed to packaging that facilitates a sterile connection and comprises an outer pouch, a lid configured to seal the outer pouch and create a sterile interior, and a component holder housed within the outer pouch, wherein the component holder comprises a board that extends longitudinally, a first set of arms extending from the board that holds a first device part, and a second set of arms extending from the board that holds a second device part.

In some embodiments, the component holder is configured to maintain an orientation of the first device part and the second device part.

In some embodiments, the component holder is configured to permit a connection between the first device part and the second device part.

In some embodiments, the component holder is configured to permit the connection between the first device part and the second device part while the outer pouch remains sealed by the lid.

In some embodiments, the component holder comprises a buckling point configured to yield in a predetermined location, bringing the first set of arms and the second set of arms closer together, when forces greater than a predetermined force act upon the component holder.

In some embodiments, the buckling point comprises a thinned section of the board of the component holder located between the first set of arms and the second set of arms.

In some embodiments, the component holder comprises a sliding portion configured to slide a first section of the board relative to a second section of the board, bringing the first set of arms and the second set of arms closer together, when forces greater than a predetermined force act upon the component holder.

In some embodiments, the sliding portion comprises the first section of the board and the second section of the board at least partially overlapping, and wherein the sliding portion is located between the first set of arms and the second set of arms.

In some embodiments, the first set of arms and the second set of arms removably hold the first device part and the second device part.

In some embodiments, the first set of arms and the second set of arms each comprise a set of two rounded arms that extend from the board.

In some embodiments, the lid comprises a planar piece of flexible material.

In some embodiments, the lid is comprised of a flexible material such that the lid is peelable from the outer pouch.

In some embodiments, the board is affixed to the lid.

In some embodiments, the outer pouch is comprised of a transparent or semi-transparent material.

In some embodiments, the transparent or semi-transparent material is capable of being deformed.

One or more embodiments of the present disclosure are directed to a method of creating a sterile connection between two or more parts, where the method comprises providing a sealed pouch containing a first device part and a second device part held in stationary positions within the sealed pouch by a component holder, pushing the first device part and the second device part together, deforming the component holder at a designed location, and creating a connection between the first device part and the second device part to create a connected part.

In some embodiments, the method comprises peeling a lid off of the sealed pouch to retrieve the component holder.

In some embodiments, the method comprises removing the connected part from the component holder.

In some embodiments, deforming the component holder comprises buckling a longitudinal board of the component holder at the designed location.

In some embodiments, deforming the component holder comprises sliding a first piece of a longitudinal board of the component holder over a second piece of a longitudinal board of the component holder at the designed location.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
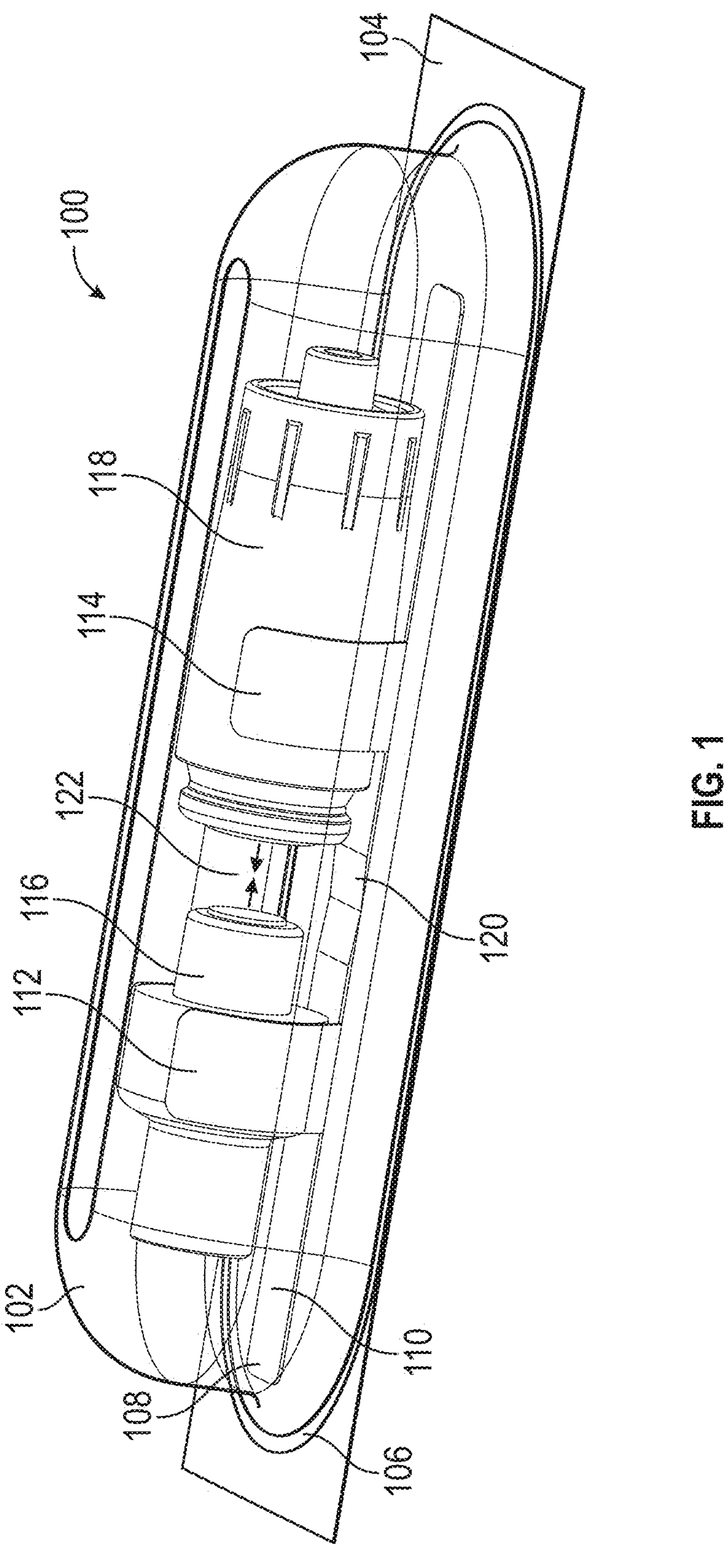
FIG. 1 shows an embodiment of a product packaging design with a designed buckling point.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of fluid connectors, such embodiments can be used in other systems that benefit from creating sterile connections. Furthermore, various applications of such embodiments and modifications thereto, which may occur to those who are skilled in the art, are also encompassed by the general concepts described herein.

The disclosed packaging facilitating sterile connections overcomes several challenges discovered with respect to certain devices such as force activated separation devices (FASD) that cannot be shipped in a fully prepared state, but that require one or more connections to be made before the device can be used. Unconnected storage is typically required for FASD to ensure there is no performance degradation. Connecting the two or more FASD may introduce contamination into the system if the devices are exposed to any potentially contaminated areas before the necessary connection between the devices is made.

Therefore, in accordance with the present disclosure, it is advantageous to provide packaging as described herein that allows for the connection of two or more parts to occur while remaining sealed within sterile packaging. This packaging design may help reduce chances of contamination and eliminate the need for any antimicrobial swabbing or other cleaning before or during device setup.

The disclosed packaging includes a pouch sealed by a lid. The packaging may use standard medical sterile barrier exterior packaging and may comprise a premade pouch or a form fill seal type pouch. Within the pouch is a disposable component holder that maintains the position of device components within the pouch during storage and shipping. The component holder allows the user to connect the two or more components by pushing them together within the pouch.

The outer pouch may be a flexible or elastic material such that a user of the packaging may be able to deform the outer pouch by pressing on it. This flexibility may allow a user to connect the device parts within the packaging pouch by pressing on the pouch material from outside the pouch to make contact with the device parts through the pouch material and manipulate the device parts without having to open the pouch. This will allow for a connection to be formed between the parts within the packaging without opening the packaging. The outer pouch material may also be substantially rigid so as to generally hold its shape when no significant forces are acted upon the pouch. The pouch, when sealed by the lid, may be filled with air or with one or more other gases. Filling the pouch to capacity or near capacity with air or gas may help the pouch keep its shape. The pouch material may also be transparent or semi-transparent to allow a user of the packaging to see through the pouch material to the contents of the pouch.

The lid may create a seal that seals off the interior of the pouch from an exterior environment. The lid may be a thin, planar piece of material. The pouch may be substantially dome shaped with a flat bottom, and the lid may be a flat piece of material that covers an opening of the pouch. The pouch may alternatively be substantially square, rectangular, or any other shape with a flat side. The lid may create a seal where the lid makes contact with an edge of the pouch. The lid may made of a flexible material. The lid may be peeled from the pouch to break the seal and open the packaging.

The component holder may comprise an elongate board that extends within the pouch of the packaging. The board may comprise a substantially stiff material such that the board may maintain its shape when subjected to nominal forces such as experienced during the shipping and handling of the packaging.

In some embodiments, the component holder may comprise arms that extend from the board. The arms may comprise protrusions that extend from edges of the board. The arms may comprise sets of two protrusions that extend from opposing edges of the board. Each set of arms may comprise a protrusion that extends upwards from one edge of the board, and another protrusion that extends upwards from an opposite edge of the board. Each of the arms may extend upwards and curve inwards. The curve of the arms may allow a device part that is substantially cylindrical to be held in place by the arms. The component holder may comprise two or more sets of arms that hold two or more device parts.

The arms of the component holder may hold two or more device parts in a particular orientation. The arms may be configured to hold two different parts that will later be pushed together, twisted together, or otherwise connected. Some parts, such as fluid connector parts, may have central axes that need to be aligned with the other fluid connector parts in order to successfully make the connection between the two parts. The arms of the component holder may hold two or more fluid connector parts such that their central axes are aligned. When the fluid connector parts are held in this alignment, the parts can simply be pushed together to make the connection between the parts, without having to otherwise align or orientate the parts. Holding the device parts in a particular orientation within the packaging can minimize the time needed to prepare the connected parts for use and minimize any errors in connecting the parts incorrectly or damage to the parts caused by improper connection.

The arms of the component holder may be thin or otherwise flexible enough to allow for the device parts to be removably held by the arms. The arms may bend to allow the device parts to be placed in the arms and removed from the arms. The arms may also be substantially rigid, so as to hold the device parts in place during shipping and storage of the packaging.

In some embodiments, instead of or in addition to arms, the component holder may comprise an adhesive, ties, or other means of holding the device parts in place against the board of the component holder.

In some embodiments, the component holder may comprise a designed buckling point that is located between two of the sets of arms. The designed buckling point may be a section of the board that is designed to be weaker than the rest of the board. The designed buckling point may comprise a section of the board that is thinner than the rest of the board, so that the integrity of the board will fail at the location of the designed buckling point when the component holder is subjected to a strong enough force. The designed buckling point may comprise two opposing sections of the board that each taper to a shared thinnest part of the board. If the component holder is subjected to a compression force, such as a user pushing together two components held by the two sets of arms, then the designed buckling point may allow the board of the component holder to buckle, break, bend, fold, or otherwise compress at the designed buckling point, allowing the user to move the two components or device parts closer together.

In some embodiments, the component holder may comprise a section of the bottom board that comprises a sliding design. The sliding design may comprise a section of the board that is located between two sets of arms and that is designed to allow a portion of the board to slide relative to another portion of the board. This design may comprise two tray components that can slide axially. This design may comprise a cutout portion of the board that another portion of the board can slide through. This design may comprise a portion of the board that is bent or curved to slide through another portion of the board. Sections of the sliding design may slide axially over each other when device parts held in the two sets of arms are pushed together. The overlap in the sections of the board caused by this sliding may allow the device parts to be pushed together while still held by the arms of the component holder.

In some embodiments, the component holder has a portion that is located between two sets of arms that is flexible or designed to bend, break, or otherwise deform in a predicted manner and a designed location in other to facilitate the connection between two device parts within the packaging while the parts are being held by the arms of the component holder.

FIG. 1 shows an exemplary product packaging 100 with a designed buckling point 120. The product packaging 100 comprises an outer pouch 102 that is sealed by a lid 104. The lid 104 creates a seal 106 that runs along an entire open edge of the outer pouch 102. A component holder 108 is located within the outer pouch 102. The component holder 108 comprises a board 110 that extends within the packaging. The board 110 comprises a first set of arms 112 and a second set of arms 114 that holds a first device part 116 and a second device part 118. The board 110 comprises a designed buckling point 120.

In some embodiments, the product packaging 100 can be used to create a sterile connection between two or more device parts, such as the first device part 116 and the second device part 118. These parts may be Force Activated Separation Devices (FASD). These parts may be shipped and stored in an unconnected state, and then connected prior to their use without having to open the packaging 100.

In some embodiments, the component holder 108 may comprise a board 110 that extends within the product packaging 100. The board 110 may provide a base for the first set of arms 112 and the second set of arms 114. The board 110 may comprise a planar or substantially flat section of material. The board 110 may adhere to lid 104. The board 110 may extend longitudinally throughout the outer pouch 102. Alternatively, the board 110 may be bent, curved, or otherwise shaped so as to allow the first set of arms 112 and the second set of arms 114 to hold the first device part 116 and the second device part 118 in a desired orientation.

In some embodiments, the first set of arms 112 and the second set of arms 114 may extend from the board 110. The first set of arms 112 and the second set of arms 114 may each comprise two arms that extend outwardly from the board 110. The two arms of each of the first set of arms 112 and the second set of arms 114 may curve inwardly, creating a rounded shape for holding the device parts.

In some embodiments, the component holder 108 may be used to keep the first device part 116 and the second device part 118 in a particular orientation prior to their connection. Component holder 108 may, for example, hold the first device part 116 relative to the second device part 118 such that a central axis of the first device part 116 aligns with a central axis of the second device part 118. If the central axes of the first device part 116 and the second device part 118 align when they are connected, then the first device part 116 and the second device part 118 can be axially pushed together to create their connection. Forces 122 acted upon the first device part 116 and the second device part 118 may push the parts together to form a connection between the parts such that the parts remain connected until a sufficient disconnection force is applied to the parts. For example, the first device part 116 may have a section that fits within a section of the second device part 118, creating a press-fit, snap-fit or other forced connection. Alternatively, the second device part 118 may have a section that fits within a section of the first device part 116 to create a connection between the parts. Alternatively, the first device part 116 and the second device part 118 may each comprise sections that interact with the other part to create a connection between the parts. Alternatively, additional parts such as, for example, a third device part, may interact with the first device part 116 and the second device part 118 to create a connection. In some embodiments, the first device part 116 and the second device part 118 can be force activated separation devices (FASD). In some embodiments, the first device part 116 and the second device part 118 are fluid connectors.

In some embodiments, the outer pouch 102 may be comprised of a flexible material such that the outer pouch 102 may be deformed by a user pushing the device parts within the packaging 100 together from outside the outer pouch 102. The outer pouch 102 may be comprised of a transparent or semi-transparent material.

In some embodiments, the lid 104 may comprise a flexible material. The lid 104 may be adhered to an edge of the pouch 102, sealing off the contents of the pouch 102 and creating a sterile interior. The lid 104 may make a seal 106 along the edge of the pouch 102 where the lid 104 contacts the pouch 102. A user of the packaging 100 may peel the lid 104 from the pouch 102 to open the packaging 100, breaking the seal 106. Alternatively, the lid 104 may comprise a stiff material, and the seal 106 may be broken by pulling apart the lid 104 and the pouch 102. In some embodiments, the board 110 of the component holder 108 is removably adhered to the face of the lid 104 that is within the borders of the seal 106 and within the contents of the pouch 102. The board 110 may be adhered to the lid 104 to prevent the component holder 108 from shifting its position within the pouch 102 during shipping and storage of the packaging 100.

In some embodiments, the board 110 has a designed buckling point 120. The designed buckling point 120 provides a location on the board 110 where a designed weakness such as a thinner section of material allows a user to more easily deform the board 110 at the designed buckling point 120. The board 110 may buckle, bend, collapse, break, or otherwise deform at the designed buckling point 120 when the user pushes the device parts together within the packaging.

Figure 2:
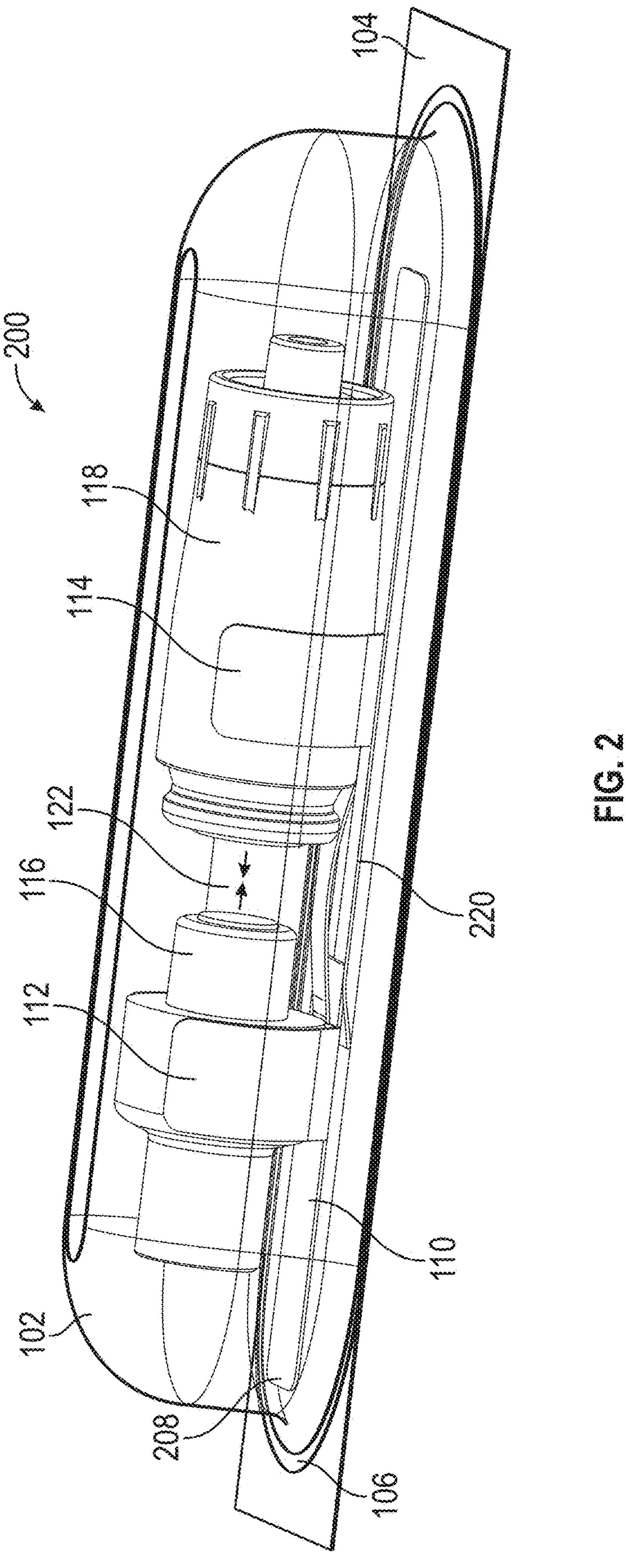
FIG. 2 shows an embodiment of a product packaging design with a sliding design.

FIG. 2 shows an exemplary product packaging 200 with a sliding design 220. The product packaging 200 comprises an outer pouch 102 that is sealed by a lid 104. The lid 104 creates a seal 106 that runs along an entire open edge of the outer pouch 102. A component holder 208 is located within the outer pouch 102. The component holder 208 comprises a board 110 that extends within the packaging. The board 110 comprises a first set of arms 112 and a second set of arms 114 that holds a first device part 116 and a second device part 118. The board 110 comprises a sliding design 220.

In some embodiments, the board 110 comprises a sliding design 220 that provides a location on the board 110 where one section of the board slides relative to another section of the board, bringing the sets of arms closer together, when a user pushes together the device parts or the sets of arms. The sections of the board that comprise the sliding design 220 may be located between the first set of arms 112 and the second set of arms 114 such that when the sections of the board within the sliding design 220 slide, the first device part 116 and the second device part 118 may be slid together to create a connection between them. The sections of the board within the sliding design 220 may slide over each other, through each other, or otherwise relative to each other in order to bring the device parts together while being held by the component holder 208.

Figure 3:
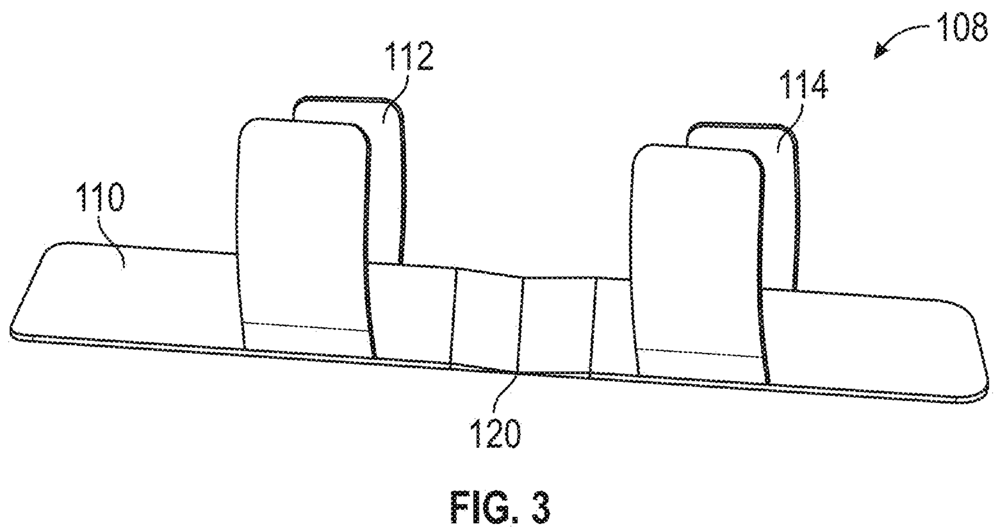
FIG. 3 shows an embodiment of a component holder with a designed buckling point.

FIG. 3 shows the component holder 108. The component holder 108 comprises the designed buckling point 120. The component holder 108 also comprises the board 110, the first set of arms 112, and the second set of arms 114.

In some embodiments, the designed buckling point 120 comprises two mirrored sections that each gradually thin to a thinnest point, as shown in FIG. 3. The thinnest point may exist in a line across the width of the board 110. The board 110 may have a thickness that becomes thinner at the designed buckling point 120. It may be possible for a user to break the component holder at the designed buckling point 120 by applying a compressive force to the component holder 108. However, it should be apparent to those of ordinary skill in the art that other similar strategically placed points of weakness or buckling points may also be alternatively used. In some embodiments, two or more buckling points may exist within the board 110 to allow the component holder 108 to compress, bringing the sets of arms suitably close enough to connect the parts held by the sets of arms.

Figure 4:
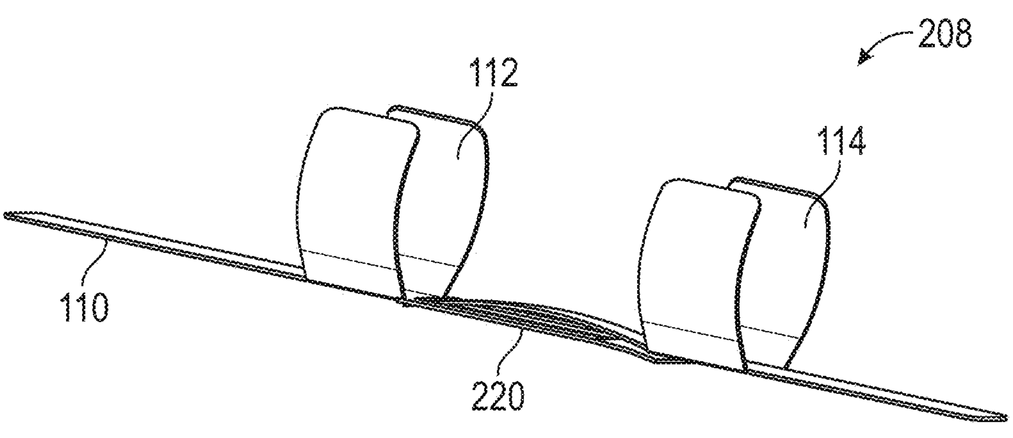
FIG. 4 shows an embodiment of a component holder with a sliding design.

FIG. 4 shows the component holder 208. The component holder 208 comprises the sliding design 220. The component holder 208 also comprises the board 110, the first set of arms 112, and the second set of arms 114.

In some embodiments, the sliding design 220 comprises a section of the board that is bent to slide over or through another section of the board, as shown in FIG. 4. The sliding design may allow the component holder 208 to slide to compress or otherwise bring the sets of arms closer together in order to facilitate making a connection between parts held in the sets of arms. However, it should be apparent to those of ordinary skill in the art that other similar sliding designs or sliding components may alternatively be used. In some embodiments, two or more sliding sections may exist within the board.

In some embodiments, the first set of arms 112 and the second set of arms 114 each comprise two arms that extend generally upwards from opposing longitudinal edges of the board, as shown. The arms in each set of arms may extend upwards from the board and curve inwards along a substantially circular profile. The shape of the arms may be such that the arms wrap around a circular perimeter of a substantially cylindrical device part. The shape of the arms may allow a cylindrical device part to be removably placed with the set of arms. The arms may hold the device part in place by wrapping around the exterior of the device part. The arms may be made of a material that is stiff enough to hold its shape when the component holder is at rest or during shipping. The arms may be made of a material that may be flexible enough to allow the device part to be placed within the arms and removed from the arms without breaking the arms. However, it should be apparent to those of ordinary skill in the art that other similar arm designs may be used. In some embodiments, three of more sets of arms may be used. In some embodiments, the arms may have a different profile shape in order to fit the device parts being held by the component holder.

The disclosures described herein include at least the following clauses:

Clause 1: Packaging to facilitate a sterile connection, the packaging comprising: an outer pouch; a lid configured to seal the outer pouch and create a sterile interior; and a component holder housed within the outer pouch, wherein the component holder comprises: a board that extends longitudinally; a first set of arms extending from the board that holds a first device part; and a second set of arms extending from the board that holds a second device part.

Clause 2: The packaging of Clause 1, wherein the component holder is configured to maintain an orientation of the first device part and the second device part.

Clause 3: The packaging of Clause 1, wherein the component holder is configured to permit a connection between the first device part and the second device part.

Clause 4: The packaging of Clause 3, wherein the component holder is configured to permit the connection between the first device part and the second device part while the outer pouch remains sealed by the lid.

Clause 5: The packaging of Clause 4, wherein the component holder comprises a buckling point configured to yield in a predetermined location, bringing the first set of arms and the second set of arms closer together, when forces greater than a predetermined force act upon the component holder.

Clause 6: The packaging of Clause 5, wherein the buckling point comprises a thinned section of the board of the component holder located between the first set of arms and the second set of arms.

Clause 7: The packaging of Clause 4, wherein the component holder comprises a sliding portion configured to slide a first section of the board relative to a second section of the board, bringing the first set of arms and the second set of arms closer together, when forces greater than a predetermined force act upon the component holder.

Clause 8: The packaging of Clause 7, wherein the sliding portion comprises the first section of the board and the second section of the board at least partially overlapping, and wherein the sliding portion is located between the first set of arms and the second set of arms.

Clause 9: The packaging of Clause 1, wherein the first set of arms and the second set of arms removably hold the first device part and the second device part.

Clause 10: The packaging of Clause 9, wherein the first set of arms and the second set of arms each comprise a set of two rounded arms that extend from the board.

Clause 11: The packaging of Clause 1, wherein the lid comprises a planar piece of flexible material.

Clause 12: The packaging of Clause 1, wherein the lid is comprised of a flexible material such that the lid is peelable from the outer pouch.

Clause 13: The packaging of Clause 1, wherein the board is affixed to the lid.

Clause 14: The packaging of Clause 1, wherein the outer pouch is comprised of a transparent or semi-transparent material.

Clause 15: The package of Clause 14, wherein the transparent or semi-transparent material is capable of being deformed.

Clause 16: A method of creating a sterile connection between two or more parts, the method comprising: providing a sealed pouch containing a first device part and a second device part held in stationary positions within the sealed pouch by a component holder; pushing the first device part and the second device part together; deforming the component holder at a designed location; and creating a connection between the first device part and the second device part to create a connected part.

Clause 17: The method of Clause 16, further comprising peeling a lid off of the sealed pouch to retrieve the component holder.

Clause 18: The method of Clause 17, further comprising removing the connected part from the component holder.

Clause 19: The method of Clause 16, wherein the deforming the component holder comprises buckling a longitudinal board of the component holder at the designed location.

Clause 20: The method of Clause 16, wherein the deforming the component holder comprises sliding a first piece of a longitudinal board of the component holder over a second piece of a longitudinal board of the component holder at the designed location.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. Packaging to facilitate a sterile connection, the packaging comprising:

an outer pouch;

a lid configured to seal the outer pouch and create a sterile interior; and a component holder housed within the outer pouch, wherein the component holder comprises:

a board that extends longitudinally;

a first set of arms extending from the board that holds a first device part;

a second set of arms extending from the board that holds an unconnected second device part with a gap disposed between the first device part and the second device part; and a buckling point configured to yield in a predetermined location to linearly move the first set of arms and the second set of arms closer together when forces greater than a predetermined force act upon the component holder, wherein the component holder is configured to permit linear movement to eliminate the gap and connect the first device part to the second device part while the outer pouch remains sealed by the lid.

2. The packaging of claim 1, wherein the component holder is configured to maintain an orientation of the first device part and the second device part.

3. The packaging of claim 1, wherein the buckling point comprises a thinned section of the board of the component holder located between the first set of arms and the second set of arms.

4. The packaging of claim 1, wherein the first set of arms and the second set of arms removably hold the first device part and the second device part.

5. The packaging of claim 4, wherein the first set of arms and the second set of arms each comprise a set of two rounded arms that extend from the board.

6. The packaging of claim 1, wherein the lid comprises a planar piece of flexible material.

7. The packaging of claim 1, wherein the lid is comprised of a flexible material such that the lid is peelable from the outer pouch.

8. The packaging of claim 1, wherein the board is affixed to the lid.

9. The packaging of claim 1, wherein the outer pouch is comprised of a transparent or semi-transparent material.

10. The package of claim 1, wherein the transparent or semi-transparent material is capable of being deformed.

11. Packaging to facilitate a sterile connection, the packaging comprising:

an outer pouch;

a lid configured to seal the outer pouch and create a sterile interior; and a component holder housed within the outer pouch, wherein the component holder comprises:

a board that extends longitudinally;

a first set of arms extending from the board that holds a first device part;

a second set of arms extending from the board that holds an unconnected second device part with a gap disposed between the first device part and the second device part; and a sliding portion configured to slide a first section of the board relative to a second section of the board, bringing the first set of arms and the second set of arms linearly closer together when forces greater than a predetermined force act upon the component holder to eliminate the gap and connect the first device part to the second device part while the outer pouch remains sealed by the lid.

12. The packaging of claim 11, wherein the sliding portion comprises the first section of the board and the second section of the board at least partially overlapping, and wherein the sliding portion is located between the first set of arms and the second set of arms.

13. A method of creating a sterile connection between two or more parts using the packaging of claim 1, the method comprising:

gripping the sealed outer pouch containing the first device part and the second device part held in stationary positions within the sealed outer pouch by the component holder;

pushing the first device part and the second device part linearly towards one another within the sealed outer pouch;

deforming the component holder at the buckling point; and creating the connection between the first device part and the second device part to create a connected part.

14. The method of claim 13, further comprising peeling the lid off of the sealed outer pouch to retrieve the component holder.

15. The method of claim 14, further comprising removing the connected part from the component holder.

16. The method of claim 13, wherein the deforming the component holder comprises buckling the longitudinal board of the component holder at the buckling point.

17. The method of claim 13, wherein the deforming the component holder comprises sliding a first piece of the longitudinal board of the component holder over a second piece of the longitudinal board of the component holder at a designed location.

* * * * *